United States Patent [19]

Kwon et al.

[11] Patent Number: 4,496,753

[45] Date of Patent: Jan. 29, 1985

[54] SAPONIFICATION OF CHLOROHYDRINS

[75] Inventors: Joon T. Kwon, Freehold Township, Monmouth County; George D. Suciu, Ridgewood, both of N.J.

[73] Assignee: Lummus Crest, Inc., Bloomfield, N.J.

[21] Appl. No.: 535,903

[22] Filed: Sep. 26, 1983

[51] Int. Cl.³ ............................................ C07D 301/26
[52] U.S. Cl. .................................... 549/521; 549/520; 549/522; 549/514
[58] Field of Search ................ 549/520, 521, 522, 514

[56] References Cited

U.S. PATENT DOCUMENTS

| | | | |
|---|---|---|---|
| 2,177,419 | 10/1939 | Engs et al. | 549/521 |
| 3,061,615 | 10/1962 | Viriot et al. | 549/521 |
| 4,008,133 | 2/1977 | Gelbein et al. | 549/521 |
| 4,443,620 | 4/1984 | Gelbein et al. | 549/521 |

FOREIGN PATENT DOCUMENTS 985405  5/1962  United Kingdom ................ 549/521

Primary Examiner—Norma S. Milestone
Attorney, Agent, or Firm—Elliot M. Olstein; John N. Bain

[57] ABSTRACT

A chlorohydrin, such as glycerol dichlorohydrin is saponified in two stages, with the first stage being carried out in a high back-mix saponification reactor, and the second stage being carried out in a plug-flow saponification reactor. The use of two different stages improves both selectivity and yield.

15 Claims, No Drawings

SAPONIFICATION OF CHLOROHYDRINS

This invention relates to the production of epoxy compounds, and more particularly to a new and improved process for producing an epoxy compound from an olefin chlorohydrin.

U.S. Pat. No. 4,008,133 discloses a process for producing an epoxy via the chlorohydrin route. In such a process, the chlorohydrin is produced by reacting an olefin with a tertiary alkyl hypochlorite and water to produce a corresponding chlorohydrin, followed by saponification of the chlorohydrin to an epoxy compound.

In accordance with the aforesaid patent, the chlorohydrin is saponified in a distillative reactor wherein the chlorohydrin is saponified simultaneously with stripping of epoxy product.

In accordance with the present invention, there is provided an improvement in a process for the saponification (dehydrochlorination) of an olefin chlorohydrin to the corresponding oxide or epoxy compound.

More particularly, in accordance with the present invention, the chlorohydrin is saponified in two stages, with the first stage being carried out in a high back-mix saponification reactor and the second stage being carried out in a plug flow saponification reactor with at least a portion of the effluent from the first stage being introduced into the second stage. Applicant has found that by employing the combination of high back-mix reactor and plug flow reactor, it is possible to increase the selectivity and yield of the saponification.

More particularly, saponification of the chlorohydrin is accomplished in separate reaction zones or reactors, with the first reaction zone or reactor being a high back-mix reactor, such as a loop reactor or a stirred tank. The second reactor is a plug flow reactor (no essential back-mixing or stirring), with the effluent from the first reactor being introduced as feed into the second reactor.

In general, in accomplishing the saponification in two reaction zones or reactors, as hereinabove described, the first reactor is operated in a manner such as to achieve from 50% to 85% of the total chlorohydrin conversion, with the remainder of the conversion being achieved in the second reactor or reaction zone, which is the plug flow reactor.

If desired, all or a portion of the epoxide produced in the first reactor can be removed (e.g., by distillation) before the first reactor effluent enters the second reactor.

The saponification is accomplished by use of a suitable base, with calcium hydroxide and sodium hydroxide being preferred. As disclosed in U.S. Pat. No. 4,008,133, the base may be supplied in admixture with another substance, such as, for example, by use of an electrolyte from a cell wherein cell liquid comprised of an aqueous solution of sodium hydroxide and sodium chloride is employed for the saponification.

In general, the saponification in each of the reaction zones is accomplished at temperatures which can vary between the freezing point and the boiling point of the mixture at the pressure of the system. Temperatures ranging between room temperature and approximately 150° C. are convenient, while the range 50°–110° C. is recommended. In each case the system should be adequate for maintaining in liquid phase the desired fraction of the reactor content. In accordance with one embodiment, different temperatures, each within the hereinabove described temperature range, may be maintained in each of the reaction zones. Thus the saponification temperature in the first zone may be higher, lower or the same as the saponification temperature in the second zone.

The back-mix reactor can have any configuration known in the art, e.g., continuous stirred tank reactor, high recirculation loop reactor, etc. The preferred configuration for the plug flow reactor is a tube which can be empty or can contain packing or similar devices in order to ensure an intimate micro-mixing between the reagents while avoiding back-mixing.

All of the base required for the reaction can be introduced into the back-mix reactor together with or separately from the chlorohydrin or, in the alternative, a portion of the base may be introduced into the back-mix reactor and the remainder into the plug-flow reactor. As should be apparent, the amount of base introduced into each of the reactors should be sufficient to achieve the desired conversion in each of the reactors.

In general, the reaction time for the back-mix reaction is less than 30 minutes, preferably from 1 to 5 minutes, and the residence time in the plug-flow reactor is less than 30 minutes, preferably from 1 to 5 minutes.

In accordance with a particularly preferred embodiment, the chlorohydrin is saponified in the presence of an inert solvent, of the type described in U.S. application Ser. No. 35,557, filed on May 3, 1979 now U.S. Pat. No. 4,443,620. The organic solvent employed in the process is inert, immiscible with the aqueous phase present in the process, and is a solvent for the chlorohydrin. The term "inert" as used herein means that the solvent does not adversely affect the reaction. As representative examples of such solvents, there may be mentioned: chlorinated hydrocarbons, including chlorinated aromatics, and chlorinated aliphatics (saturated); e.g., chlorobenzene, chlorinated parafins, such as carbon tetrachloride, chloroform, dichloropropane, etc.; chlorinated ethers; and the like. Such solvents may be employed alone or as a mixture of two or more thereof. The use of such a solvent in combination with the two different reaction zones particularly increases selectivity.

Thus, the saponification may be accomplished with a wide variety of materials and in a wide variety of ways, provided that the saponification is accomplished in separate reaction zones (each zone containing at least one reactor), with the first reaction zone being a high back-mix reaction zone, and the second zone being a plug-flow reaction zone.

As should be apparent, in accordance with the present invention, the initial portion of the saponification is performed under conditions of high back-mixing (for example, a stirred tank), and the saponification is completed under plug-flow (pipeline flow) conditions. The initial back-mix portion may be accomplished in more than one reactor, and, similarly, the final plug-flow portion may be accomplished in more than one reactor. Similarly, as hereinabove described, all, a portion, or none of the epoxy compound produced in the initial back-mix portion may be recovered prior to initiating the final plug-flow portion of the saponification. Similarly, as hereinabove noted, all or a portion of the base requirements may be introduced into the initial back-mix portion, provided that there is sufficient base present in the initial back-mix portion to achieve the desired conversion in such portion.

The chlorohydrins which may be saponified in accordance with the present invention, may be represented by the following structural formula:

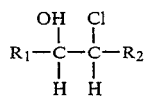

wherein $R_1$ and $R_2$ are each separately either hydrogen; alkyl; halo, naphthyl, or phenyl substituted alkyl; phenyl or alkyl substituted phenyl; phenyl; naphthyl; halo or alkyl substituted naphthyl; alkenyl or halo substituted alkenyl; and $R_1$ and $R_2$ can be linked together to provide a cycloalkene (generally 5 to 10 carbon atoms). The alkyl and alkenyl groups generally contain 1 to 6 carbon atoms and the halo group is preferably iodo, bromo or chloro, most preferably chloro. As representative examples of the most suitable feeds to the saponification, there may be mentioned: propylene chlorohydrin (a chlorohydrin which may be derived from propylene) and glycerol dichlorohydrin (a chlorohydrin which may be derived from allyl chloride).

The saponification of the present invention may be incorporated into an overall process for producing an epoxy compound, such as disclosed, for example, in U.S. Pat. No. 4,008,133, wherein such production is integrated with a cell electrolysis process for producing chlorine.

In accordance with the present invention, the main saponification reactor is a high back-mix reactor; however, this reactor may be smaller than those which would be employed in the case where the only reactor is a high back-mix reactor in that in accordance with the process of the invention there is a shorter contact time in the first reactor. The secondary reactor could be a simple transfer line of appropriate dimensions or a heat exchanger of the coil type, and as hereinabove described, shorter contact times are employed in such reactors.

As a further advantage of the present invention, it has been found that the waste water produced in the saponification has a lower total organic carbon content than that which results from saponification in accordance with prior art procedures. The lowering of the total organic carbon content of the waste water reduces the treatment required for lowering the content of total organics.

By proceeding in accordance with the two reactors of the present invention, it is possible to achieve high selectivity, at high conversions, and at short reaction times, while reducing the total organic content of the waste water produced in the saponification. In particular, by proceeding in accordance with the present invention, it is possible to achieve essentially complete conversion of the base and generally at least 90%, and up to 99% conversion of the chlorohydrin, at selectivities to the desired epoxide of 96–98+ mole %, while maintaining the total organic content of the waste water below 3000 ppm, and preferably below 1500 ppm.

The invention will be further described with respect to the following examples; however, the scope of the invention is not to be limited thereby:

EXAMPLES 1 TO 5

The organic feed to be saponified is 28.2% by weight of glycerol dichlorohydrins in carbon tetrachloride (density at 23° C. is 1.4608 gram/cc). The aqueous caustic feed is 8.45 weight percent of sodium hydroxide in water (density at 23° C. is 1.1896 grams/cc). The organic and caustic feeds are each separately preheated to 80° C. and separately introduced into a high back-mix (recycle-loop) reactor. The high back-mix reactor has a volume of 25 cc. The recirculation flow in the loop is 400 cc per minute. The reactor is made of stainless steel tubing.

The reactor is operated with a feed volume contact time of from 1.2 to 2.4 minutes.

The effluent from the high back-mix reactor is introduced into a plug-flow reactor made of an empty Teflon tube having a length to diameter ratio longer than 100/1. The contact time in the plug-flow reactor was 1.2 to 2.5 minutes. Both reactors were kept at 80° C. A pressure of 2.2 to 3.5 atmospheres was maintained by means of a back-pressure regulator.

The test results are listed in Table I.

EXAMPLES 6 TO 9

Example 1 was repeated. Different reaction temperatures were maintained in the two reactors for further enhancement of saponification rate. Process conditions are as follows:

| Example Number | 6 | 7 | 8 | 9 |
|---|---|---|---|---|
| Temp. °C. (Loop/Pipe) | 80/65 | 80/65 | 65/80 | 65/80 |
| Contact Time, min. (Loop) | 1.20 | 1.19 | 1.16 | 1.79 |
| Contact Time, min. (Pipe) | 1.25 | 2.48 | 3.59 | 5.52 |

TABLE I
Glycerol
Saponification of Propylene Dichlorohydrins

| Example No. | Mass Balance (%) | | NaOH/DCH (% mole) | | Conversions (% mole) | | Selectivities in Products (% mole) | | | | TOC in Brine (ppm) |
|---|---|---|---|---|---|---|---|---|---|---|---|
| | Weight | DCHs | Charged | Consumed | NaOH | DCHs | Epi. | Glycidol | Ethers | Glycerol | |
| 1 | 99.21 | 98.79 | 99.09 | 99.09 | 99.22 | 87.88 | 97.12 | 0.05 | 0.02 | 2.81 | 1913 |
| 2 | 98.15 | 91.51 | 98.81 | 98.81 | 98.49 | 89.66 | 96.94 | 0.04 | 0.02 | 3.00 | 1864 |
| 3 | 98.99 | 92.15 | 99.89 | 99.89 | 99.59 | 90.25 | 96.28 | 0.05 | 0.16 | 3.51 | 2225 |
| 4 | 97.92 | 97.93 | 100.08 | 100.08 | 99.40 | 92.15 | 95.68 | 0.06 | 0.05 | 4.21 | 2907 |
| 5 | 98.62 | 99.52 | 101.07 | 101.07 | 99.77 | 72.79 | 97.75 | 0.05 | 0.07 | 2.13 | 1440 |
| 6 | 98.66 | 99.70 | 104.31 | 104.31 | 96.86 | 71.37 | 97.54 | 0.02 | 0.34 | 2.10 | 1357 |
| 7 | 99.36 | 95.58 | 101.49 | 101.49 | 97.63 | 80.96 | 97.67 | 0.03 | 0.17 | 2.12 | 1339 |
| 8 | 99.60 | 101.34 | 102.33 | 102.33 | 99.19 | 83.81 | 97.65 | 0.02 | 0.33 | 2.01 | 1376 |

TABLE I-continued

| | | | | | | | | | | |
|---|---|---|---|---|---|---|---|---|---|---|
| | colspan="10" | Glycerol Saponification of Propylene Dichlorohydrins | | | | | | | | |
| Example | Mass Balance (%) | | NaOH/DCH (% mole) | | Conversions (% mole) | | Selectivities in Products (% mole) | | | | TOC in Brine |
| No. | Weight | DCHs | Charged | Consumed | NaOH | DCHs | Epi. | Glycidol | Ethers | Glycerol | (ppm) |
| 9 | 98.16 | 95.98 | 102.68 | 102.68 | 99.73 | 83.63 | 97.17 | 0.06 | 0.17 | 2.60 | 1703 |

DCH — mixture of 1,3- and 2,3- glycerol dichlorohydrins.
Epi — epichlorohydrin.
Ethers — mixture of chlorinated alkyl ethers, present as impurities in the DCH.
TOC — tolol organic carbon.
* calculated in terms of moles of DCH.

The present invention is particularly advantageous in that it permits saponification of a chlorohydrin at high conversion, high selectivity, and in short reaction times with essentially complete conversion of the base. The two-stage reactor system is simpler, smaller, and easier to operate than the reactors applied in the art for saponification of chlorohydrins. In addition, waste water from the saponification has a lower total organic content than known in the art. These and other advantages should be apparent to those skilled in the art from the teachings herein.

Numerous modifications and variations of the present invention are possible in light of the above teachings and, therefore, within the scope of the appended claims the invention may be practiced otherwise than as described.

What is claimed is:

1. In a process for the saponification of a chlorohydrin to an epoxy compound with an aqueous base, the improvement comprising:
   saponifying the chlorohydrin in a first and second stage, said first stage being under high back-mix conditions, said second stage being under plug-flow conditions, and at least a portion of the effluent from the first stage being introduced into the second stage.

2. The process of claim 1 wherein the entire effluent from the first stage is introduced into the second stage.

3. The process of claim 1 wherein at least a portion of the epoxy compound present in the effluent from the first stage is separated from the effluent prior to introduction into the second stage.

4. The process of claim 1 wherein a portion of the base employed in the saponification is introduced into the first stage and the remaining portion is introduced into the second stage.

5. The process of claim 1 wherein all of the base is introduced into the first stage.

6. The process of claim 1 wherein the chlorohydrin is saponified in an inert organic solvent which is immiscible with the aqueous base.

7. The process of claim 6 wherein the first and second stages are operated at different temperatures.

8. The process of claim 1 wherein from 50% to 85% of the chlorohydrin is converted in the first stage.

9. The process of claim 8 wherein the residence time in each of the first and second stages is from 1 to 5 minutes.

10. The process of claim 9 wherein the saponification temperature in the first stage is from 50° C. to 110° C. and the saponification temperature in the second stage is from 50° C. to 110° C.

11. The process of claim 10 wherein the chlorohydrin is glycerol dichlorohydrin.

12. In a process for the saponification of glycerol dichlorohydrin to epichlorohydrin with an aqueous base in the presence of an inert organic solvent which is immiscible with the aqueous base, the improvement comprising:
    effecting said saponification in first and second saponification stages, said first saponification stage being operated at a residence time of less than 30 minutes and under high back-mix conditions and the second stage being operated at a residence time of less than 30 minutes and under plug-flow conditions, with at least a portion of first stage effluent being introduced into the second stage, from 50% to 85% of the glycerol dichlorohydrin being converted in the first stage and the total conversion being at least 90%.

13. The process of claim 12 wherein the saponification temperature in the first stage is from 50° C. to 110° C. and the saponification temperature in the second stage is from 50° C. to 110° C.

14. The process of claim 13 wherein the residence time in each of the first and second stages is from 1 to 5 minutes.

15. The process of claim 14 wherein the first and second stages are operated at different temperatures.

* * * * *